(12) United States Patent
Hening et al.

(10) Patent No.: US 9,897,548 B2
(45) Date of Patent: Feb. 20, 2018

(54) METHOD AND APPARATUS FOR DETECTION OF CONTAMINANTS IN AIR BY LASER-INDUCED FILAMENTATION

(71) Applicant: The United States of America as represented by the Secretary of the Navy, Washington, DC (US)

(72) Inventors: Alexandru Hening, San Diego, CA (US); Robert George, Chula Vista, CA (US); Ronald Wroblewski, San Diego, CA (US); Scott McGirr, San Diego, CA (US)

(73) Assignee: The United States of America as represented by Secretary of the Navy, Washington, DC (US)

( * ) Notice: Subject to any disclaimer, the term of this patent is extended or adjusted under 35 U.S.C. 154(b) by 0 days.

(21) Appl. No.: 15/232,616

(22) Filed: Aug. 9, 2016

(65) Prior Publication Data

US 2017/0045458 A1 Feb. 16, 2017

Related U.S. Application Data

(60) Provisional application No. 62/203,727, filed on Aug. 11, 2015.

(51) Int. Cl.
*G01N 21/71* (2006.01)
*G01N 21/17* (2006.01)
*G01N 21/94* (2006.01)

(52) U.S. Cl.
CPC ........... *G01N 21/718* (2013.01); *G01N 21/94* (2013.01); *G01N 2021/1712* (2013.01); *G01N 2201/06113* (2013.01)

(58) Field of Classification Search
CPC ................. G01N 21/718; G01N 21/94; G01N 2021/1712; G01N 2201/06113
See application file for complete search history.

(56) References Cited

U.S. PATENT DOCUMENTS

2002/0141471 A1* 10/2002 Aab ...................... H01S 3/0811
372/57
2016/0266466 A1* 9/2016 Milchberg ............ G02F 1/3511

OTHER PUBLICATIONS

I.C.E. Turco, I.N. Ross, M.S. Schulz, H. Daido, G.J. Tallents, J. Krishnan, L. Dwivedi, A. Hening "Spatial Coherence Measurements and X-Ray Holographic Imaging Using a Laser-Generated Plasma X-ray Source in the Water Window Spectral Region." Journal of Applied Physics, 73, 8081 (1993).
I. Apostal, D. Craciun, M. Ristici, D. Apostol, A. Hening et. al. "Laser Produced Cadmium Plasma as a Laser Source." Proc. SPIE 1033, Tends in Quantum Electronics, 2 (May 18, 1989).

(Continued)

*Primary Examiner* — Christine Sung
(74) *Attorney, Agent, or Firm* — SPAWAR Systems Center Pacific; Kyle Eppele; Susanna J. Torke

(57) ABSTRACT

A method using a laser to propagate a laser beam through an optically-transparent medium, wherein the laser has a power level beyond a critical value $P_{cr}$, and wherein the laser beam interacts with the optically transparent medium to generate a laser-induced plasma filament (LIPF); and adjusting the power level to qualitatively detect chemical components within the optically-transparent medium.

17 Claims, 5 Drawing Sheets

(56) References Cited

OTHER PUBLICATIONS

I. Ursu, I. Apostol, M. Dinescu, A. Hening, et. al "Threshold Conditions for the Air Plasma Initiation Near Solid Surfaces Under the Action of Powerful Pulsed CO2 Laser Radiation." Journal of Applied Physics, 58, 1765 (1985).
Couairon "Filamentation length of powerful laser pulses" Applied Physics B, 76, 789 (2003).
M.H. Helle, T.G. Jones, J.R. Penano, D. Kaganovich, A. Ting "Formation and Propagation of Meter-Scale Filaments in Water." Applied Physics Letters, 103, 121101 (2013).
R. Ackerman, G. Mejean, J. Kasparian, J. Yu, E. Salmon, J.P. Wolf "Laser Filaments Generated and Transmitted in Highly Turbulent Air." Opt. Letters, 31 (2006) 86-88.

\* cited by examiner

METHOD AND APPARATUS FOR DETECTION OF CONTAMINANTS IN AIR BY LASER-INDUCED FILAMENTATION

CROSS-REFERENCE TO RELATED APPLICATIONS

This application claims the benefit of U.S. Provisional Patent Application Ser. No. 62/203,727, filed on Aug. 11, 2015, the entire content of which is fully incorporated by reference herein.

FEDERALLY-SPONSORED RESEARCH AND DEVELOPMENT

The Method and Apparatus for Detection of Contaminants in Air by Laser Induced Filamentation is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-5118; email ssc_pac_T2@navy.mil. Reference Navy Case Number 103305.

BACKGROUND

Laser-based spectroscopy has been used for sensing atmospheric species. However, conventional remote-sensing techniques require coherent tunable sources, which do not provide enough power for remote detection. The transmission characteristics of important contaminants are often only subtly different from the air at low power, making remote detection difficult. In the presence of contaminants, plasma is generated due to the high intensity electromagnetic field. Described herein is a method for detection of contaminants in air by using the process of laser-induced plasma filamentation (LIPF).

DETAILED DESCRIPTION OF SOME EMBODIMENTS

Reference in the specification to "one embodiment" or to "an embodiment" means that a particular element, feature, structure, or characteristic described in connection with the embodiments is included in at least one embodiment. The appearances of the phrases "in one embodiment", "in some embodiments", and "in other embodiments" in various places in the specification are not necessarily all referring to the same embodiment or the same set of embodiments.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or.

Additionally, use of the "a" or "an" are employed to describe elements and components of the embodiments herein. This is done merely for convenience and to give a general sense of the invention. This detailed description should be read to include one or at least one and the singular also includes the plural unless it is obviously meant otherwise.

Figure 1:
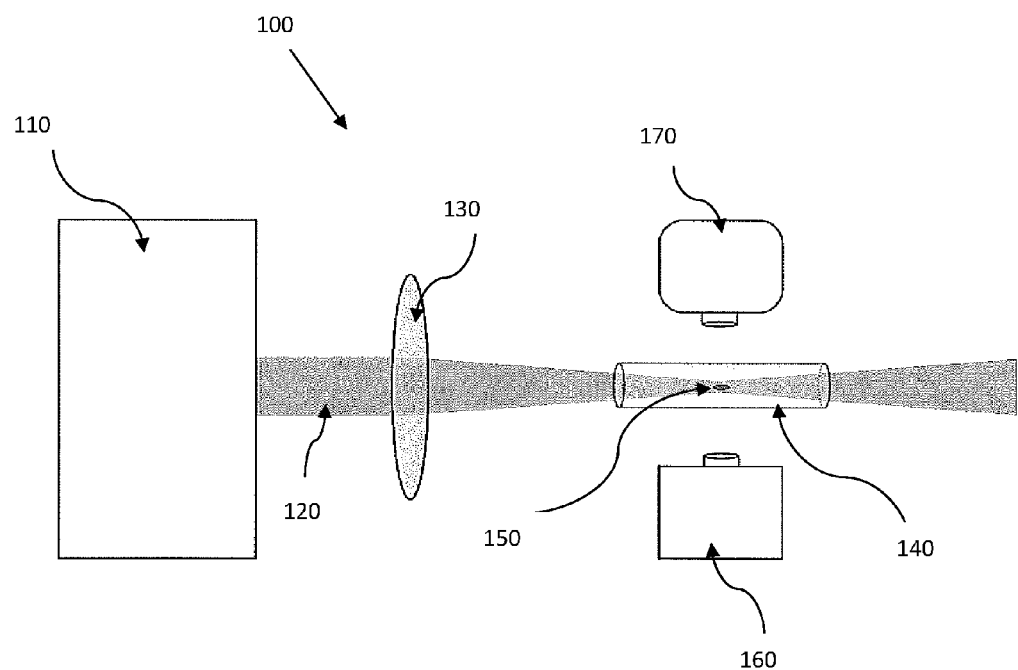
FIG. 1 shows a schematic view of an experimental setup in accordance with the method and apparatus for detection of contaminants in air by laser induced filamentation.

FIG. 1 shows a schematic of an experimental set-up of a system 100 in accordance with the method and apparatus for detection of contaminants in air by laser induced filamentation. To the left is the beam source: a KrF excimer laser 110 operating at 248 nm, the source of beam 120. Beam 120 is focused through a lens 130 into a containment cell 140 with UV windows. A short plasma 150 is generated at the beam focus and imaged with an optical camera 160 and an infrared (IR) camera 170. Excimer laser 110 can deliver 400 mJ per pulse. The pulses are 20 ns in duration and have a repetition rate of up to 10 Hz. It has a peak power of 20 MW. This is far below the critical power for air at 248 nm: 180 MW, but well above that for aqueous media: 1.7 MW. The output beam 120 width is 3×2 cm, which is then focused roughly to 10 µm. If there are no contaminants, nothing should be visible. Only by using a solid target, one can measure the focal spot (the dimension of the focused laser beam). In the presence of contaminants, plasma is generated due to the high intensity electromagnetic field.

Figure 2:
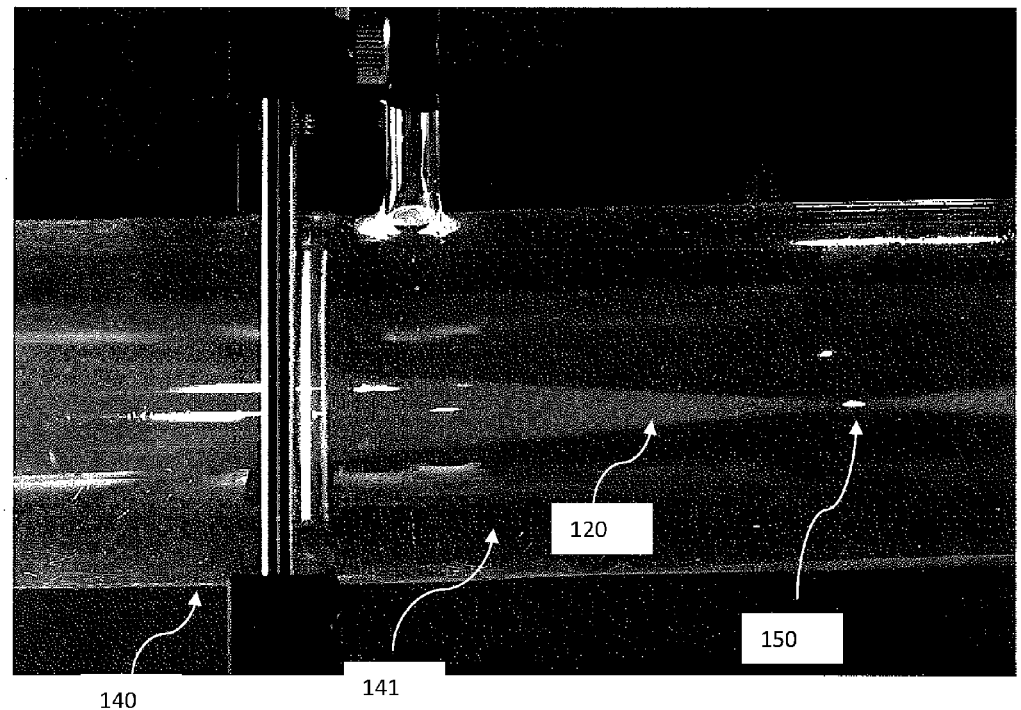
FIG. 2 shows a solvent-containment cell showing laser-beam focusing, attenuation, and plasma generation in accordance with the method and apparatus for detection of contaminants in air by laser induced filamentation.

FIG. 2 shows a close-up view of a section of containment cell 140. The dimensions of containment cell 140 are 62 mm in width and 500 mm in length. Containment cell 140 has a contained solvent 141. Contained solvent 141 is volatile vapor mixture of hexane, acetone, and methanol, which visibly attenuates and scatters focusing beam 120 both before and after plasma point 150. The laser-induced plasma filaments (LIPF) can range in length up to 5 cm. The induced plasma 150 is clearly visible at the beam 120 focus point.

Laser-beam propagation through the atmosphere is influenced by many system parameters such as excitation energy, temporal and spatial beam profile, wavelength, repetition rate (or continuous wave operation), etc. Laser-beam propagation is dependent on atmosphere composition and density that is affected by region, elevation, and temperature. The characteristics of the induced filamentation, particularly its spatial distribution and temporal evolution, are important parameters to be considered in the ultimate success or failure of the method disclosed herein. LIPFs are generated in transparent media when the laser power goes beyond a critical power $P_{cr}$.

$$P_{cr.} = \frac{3.37\lambda^2}{8\pi n_0 n_2} \quad \text{(Eq. 1)}$$

Here, $\lambda$ is the wavelength of the laser source, $n_0$ is linear refractive index, and $n_2$ is nonlinear refractive index.

Filamentation is a process involving two competing effects: intensity-driven self-focusing and ionization-driven defocusing. It has been shown that self-focusing occurs when the laser power exceeds the critical-power threshold. Beyond that value, the intensity-dependent refractive index enables the pulse to overcome the natural diffraction spreading and begin to self-focus. This effect is the crucial element in filament formation. It is a third order nonlinear optical process known as the optical Kerr Effect and is due to the intensity-dependent index of refraction. The optical Kerr Effect is the crucial element in filament formation, enabling the pulse to overcome natural diffractive spreading:

$$n_I = n_0 + n_2 I(r,t) \quad \text{(Eq. 2)}$$

where $I(r,t)$ is the intensity profile of the laser pulse, $n_0$ is optically transparent media, (air or a mixture of air and contaminants vapors), and $n_2$ is the nonlinear refractive index. For a vacuum $n_2 = 1.0*10^{-34}$ (vacuum), for air $n_2 = 5.0*10^{-1}$, and for water $n_2 = 4.1*10^{-16}$. The LIPF generated will increase the dispersion of the beam due to its high density of electrons and ions. The net result is a propagation of the focusing-defocusing cycles. Each plasma dot forms a part of a long filament, which can extend a few hundreds of meters.

The onset of filamentation at certain values of laser power will signal the presence of contaminating aerosols. This method will qualitatively detect chemical components, especially vapors of volatile contaminants in air, by adjusting the power level of the laser. Often these contaminants have a significantly larger $n_2$ than air, and hence a significantly lower power threshold to achieve filamentation. Thus, one can remotely induce and observe filamentation in contaminated air rather than clean air, at least qualitatively. An advantage of this method is its ability to burn through turbulence, a significant issue with conventional systems. Alternate embodiments would allow for quantitative remote analyses as well.

Two competing physical processes are involved in laser beam propagation: self-focusing due to optical Kerr effect and optical diffraction. The index of refraction of air is affected by the presence of an intense electromagnetic field (which is associated to the laser beam). That can lead to a lens-like effect and the laser beam will be focused due to the fact that the wave front is changing the index of refraction. The LIP generated will increase the dispersion of the beam due to its high density of electrons and ions, having a net result of propagation of the focusing-defocusing cycles. Each plasma dot, as part of a long filament which can extend few hundreds of meters, can perform from the tangible air vehicle. The LIPF will be detectable over a wide spectral range from IR to extreme UV.

Figure 3:
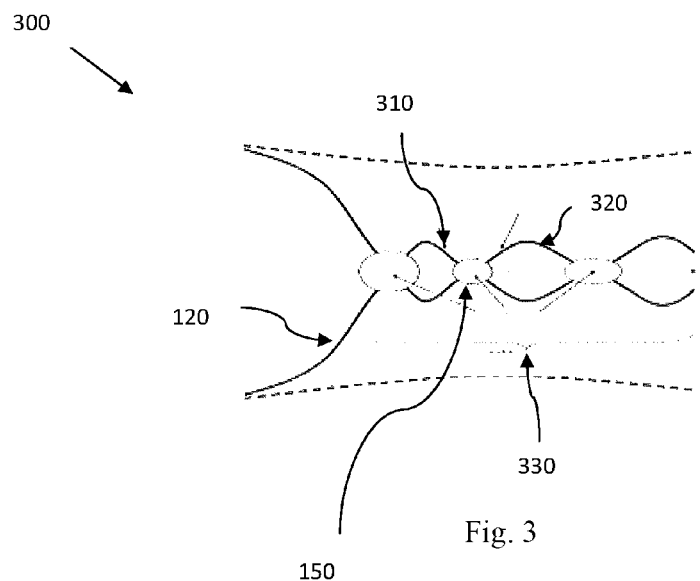
FIG. 3 shows a side view of a laser induced plasma filament in accordance with the method and apparatus for detection of contaminants in air by laser induced filamentation.

FIG. 3 shows an illustration of a laser induced plasma filament (LIPF) 300. LIPF 300 generated will increase the dispersion of beam due 120 to its high density of electrons and ions, having a net result a net propagation of the focusing 310 and defocusing 320 cycles, resulting in filament 330. Each plasma dot, as part of a long filament which can extend a few hundreds of meters, can perform as a decoy flare, its spectral range emission extending from infrared to extreme ultra-violet.

Figure 4:
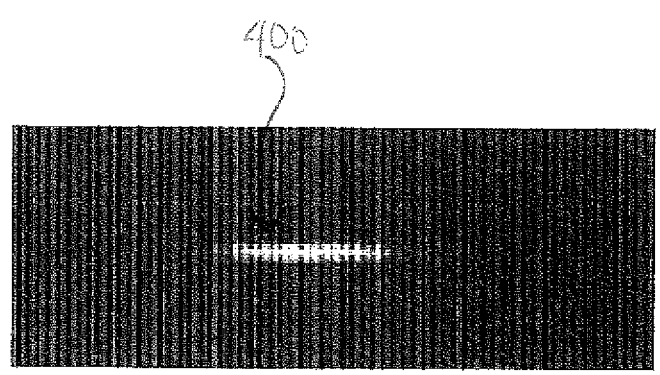
FIG. 4 shows a laser induced plasma in air in accordance with the method and apparatus for detection of contaminants in air by laser induced filamentation.

FIG. 4 shows a recorded infrared image of a laser induced plasma (LIP) 400 in air, which was generated using a 248 nm KrF excimer laser (not visible here).

Figure 5:
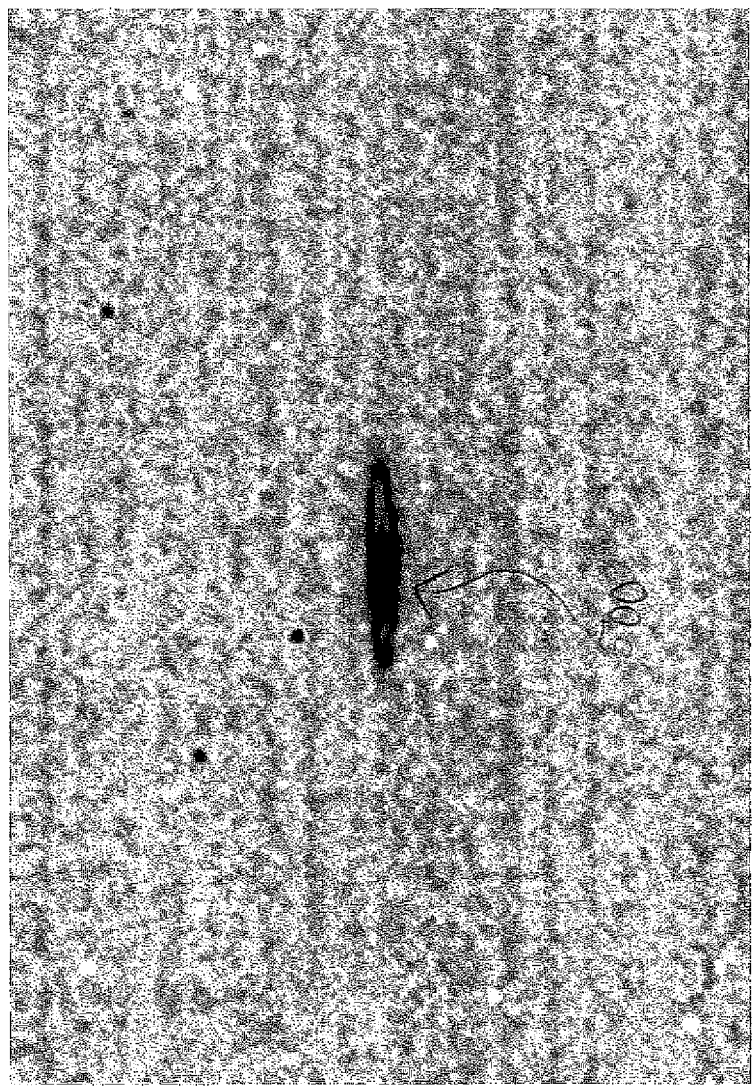
FIG. 5 shows an infrared image of a laser induced plasma in air in accordance with the method and apparatus for detection of contaminants in air by laser induced filamentation.

FIG. 5 shows a plasma 500 in infrared that was generated using a volatile vapor mixture in a containment cell not visible here.

Figure 6:
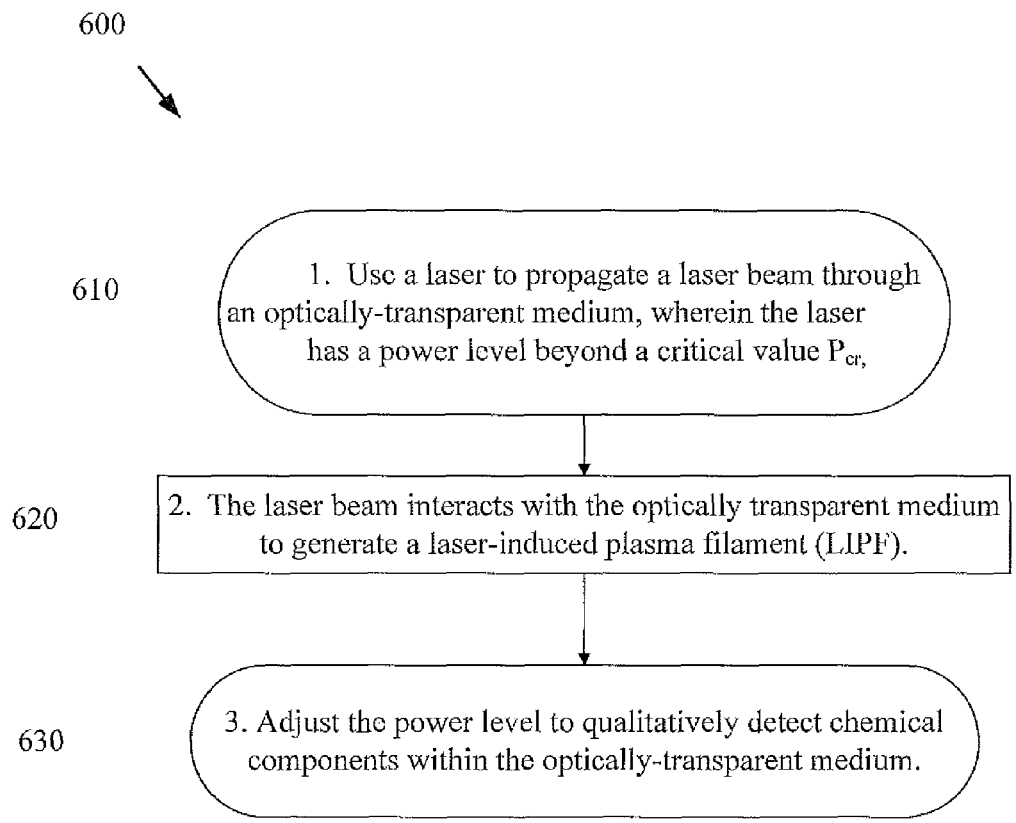
FIG. 6 shows an embodiment of a method in accordance with the method and apparatus for detection of contaminants in air by laser induced filamentation.

FIG. 6 shows an embodiment of a method 600 in accordance with the method and apparatus for detection of contaminants in air by laser induced filamentation. Method 600 may begin at step 610, wherein a laser is used to propagate a laser beam through an optically-transparent medium, wherein the laser has a power level beyond a critical value $P_{cr}$. Step 620 involves the laser beam interacting with the optically transparent medium to generate a laser-induced plasma filament (LIPF). Step 630 involves adjusting the power level to qualitatively detect chemical components within the optically-transparent medium.

An advantage of the disclosed embodiment is the speed of deployment; compared to traditional techniques which require tens of seconds, the response time is of the order of millionths of seconds. The laser beam propagates with the speed of light and the ionization process requires few nanoseconds. In addition, the proposed system can cover a wide spectrum of chemicals by using a single laser source we can switch from infrared to ultraviolet. It confers a high degree of flexibility and adaptability; the system can be easily re-configured to match future materials and sensor development. Use requires only an operator to point out the approximate position of the area of interest and scan it.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method comprising the steps of:
   using a laser to propagate a laser beam through an optically-transparent medium, wherein the laser has a power level beyond a critical value Pcr;
   adjusting the power level to a certain power level such that the laser beam interacts with the optically transparent medium to generate a laser-induced plasma filament (LIPF); and
   using a camera to detect the LIPF, wherein generation of the LIPF at the certain power level signals the presence of chemical components within the optically-transparent medium.

2. The method of claim 1 wherein the chemical components are vapors of volatile contaminants.

3. The method of claim 2 wherein the vapors are a mixture of hexane, acetone, and methanol.

4. The method of claim 3 wherein $P_{cr}=3.37\lambda^2/(8\pi n_0 n_2)$, wherein $\lambda$ is the wavelength of the light source, $n_0$ is the linear refractive index of the laser beam, and $n_2$ is the nonlinear refractive index of the laser beam.

5. The method of claim 4, wherein the optically-transparent medium is air.

6. The method of claim 5 wherein the laser beam is switchable from infrared to ultraviolet.

7. The method of claim 6 wherein the laser is an excimer laser.

8. A method for detecting contaminants comprising the steps of:
  using a laser to generate laser-induced plasma filaments in optically-transparent medium, wherein the laser comprises a beam, a light source, and a power value,
  wherein the laser power value goes higher than a critical power value $P_{cr}$,
  wherein the critical power value depends on the wavelength of the light source, the laser beam, and the optical parameters of the medium, and
  wherein the plasma filaments are generated at a certain laser power value, and the laser power value is adjusted to the certain laser power value to generate the plasma filaments; and
  using a camera to detect the plasma filaments, wherein generation of the plasma filaments at the certain power level signals the presence of chemical components within the optically-transparent medium.

9. The method of claim 8 wherein the optically-transparent medium is air.

10. The method of claim 9 wherein the laser is an excimer laser.

11. The method of claim 10 wherein the contaminants are volatile vapors.

12. The method of claim 11 wherein the vapors are a mixture of hexane, acetone, and methanol.

13. The method of claim 12 wherein the laser beam is switchable from infrared to ultraviolet.

14. A system comprising:
  a laser configured to generate a laser-induced plasma filament within an optically-transparent medium, wherein the laser has an adjustable laser power, and the laser power goes beyond a critical value $P_{cr}$,
  wherein the plasma filament is generated at a certain laser power value, and the laser power is adjusted to the certain laser power value to generate the plasma filaments; and
  a camera configured to detect the plasma filament, wherein generation of the plasma filaments at the certain power level signals the presence of chemical components within the optically-transparent medium.

15. The system of claim 14, wherein the laser is configured to generate the laser-induced plasma filament using a plurality of high-power, ultra-short pulses.

16. The system of claim 15, wherein the laser is an excimer laser.

17. The system of claim 16, wherein the laser is configured to be switchable between ultraviolet and infrared.

* * * * *